(12) United States Patent
Ghosh

(10) Patent No.: US 9,861,657 B2
(45) Date of Patent: *Jan. 9, 2018

(54) TREATMENT OF BONE MARROW EDEMA (OEDEMA) WITH POLYSULFATED POLYSACCHARIDES

(71) Applicant: PARADIGM HEALTH SCIENCES PTY LTD, Fairlight, New South Wales (AU)

(72) Inventor: Peter Ghosh, Fairlight (AU)

(73) Assignee: PARADIGM HEALTH SCIENCES PTY LTD, Fairlight, New South Wales (AU)

(*) Notice: Subject to any disclaimer, the term of this patent is extended or adjusted under 35 U.S.C. 154(b) by 0 days.

This patent is subject to a terminal disclaimer.

(21) Appl. No.: 14/790,476

(22) Filed: Jul. 2, 2015

(65) Prior Publication Data
US 2015/0297633 A1 Oct. 22, 2015

Related U.S. Application Data

(63) Continuation of application No. 13/983,406, filed as application No. PCT/AU2012/000091 on Feb. 2, 2012, now Pat. No. 9,101,650.

(30) Foreign Application Priority Data

Feb. 2, 2011 (AU) ................................ 2011900325

(51) Int. Cl.
*A61K 31/737* (2006.01)
*A61K 9/00* (2006.01)

(52) U.S. Cl.
CPC .......... *A61K 31/737* (2013.01); *A61K 9/0019* (2013.01)

(58) Field of Classification Search
CPC ............................ A61K 31/737; A61K 9/0019
See application file for complete search history.

(56) References Cited

FOREIGN PATENT DOCUMENTS

| CN | 1476328 A | 2/2004 |
|---|---|---|
| WO | WO 02/41901 A1 | 5/2002 |
| WO | WO 2009/070842 | 6/2009 |

OTHER PUBLICATIONS

Hoffman et al., Bone marrow edema in the knee. Differential diagnosis and therapeutic possibilities, Der Orthopade 4, 2006, pp. 463-477.
Ghosh et al., Effects of Pentosan Polysulfate in Osteoarthritis of the Knee: A Randomized, Double-Blind, Placebo-Controlled Pilot Study, Current Therapeutic Research, vol. 66, No. 6, Nov./Dec. 2005, pp. 552-571.
Ghosh, The Pathobiology of Osteoarthritis and the Rationale for the Use of Pentosan Polysulfate for Its Treatment, Seminars in Arthritis and Rheumatism, vol. 28, No. 4, Feb. 1999, pp. 211-267.
Extended European Search Report dated Jun. 8, 2015 for PCT/AU2012/000091, Applicant Paradigm Health Sciences Ltd Pty.
Bartl et al.; "Treatment of bone marrow edema syndrome with intravenous Ibandronate;" Archives of Orthopaedic and Trauma Surgery; Springer (2012); 9 pages.
Deangelis et al.; "Traumatic Bone Bruises in the Athlete's Knee;" Sports Health: vol. 2, No. 5; Sep. 2010; 7 pages.
Elias et al.; "Bone stress injury of the ankle in professional ballet dancers seen on MRI;" BMC Musculoskelet Disord. (2008), vol. 9, No. 39; 7 pages.
Ghosh et al, Current Therapeutic Research, 2005, 66(6), p. 552-571.
Ghosh, Seminars in Arthritis and Rheumatism, 1999, 28(4), p. 211-267.
Hayes et al, "MR Imaging of Bone Marrow Edema. Pattern: Transient Osteoporosis, Transient Bone Marrow Edema Syndrome, or Osteonecrosis", RadioGraphics, 1993, 13, p. 1001-1011.
Kijowski et al, Radiology, 2006, 238(3), p. 943-949.
Marlovits et al, European Journal of Radiology, 2004, 52, p. 310-319.
Meizer et al.; "Outcome of painful bone marrow edema of the femoral head following treatment with parenteral iloprost;" Indian J. Orthop. (2009); vol. 43, No. 1; 7 pages.
Wenham et al.; "Imaging the painful osteoarthritic knee joint: what have we learned?" Nature Clinical Practice Rheumatology (2009), vol. 5, No. 3; pp. 149-158.
Zoga et al.; "Musculoskeletal Imaging: MR Imaging of Athletic Pubalgia and Sports Hernia;" Radiology: vol. 247, No. 3; (Jun. 2008); pp. 797-807.

*Primary Examiner* — Jonathan S Lau
(74) *Attorney, Agent, or Firm* — Thorpe North & Western

(57) ABSTRACT

A method for the treatment of bone marrow edema in a mammal comprising administering an effective amount of a polysulfated polysaccharide including salts thereof, to a mammal in need of such treatment.

6 Claims, 2 Drawing Sheets

TREATMENT OF BONE MARROW EDEMA (OEDEMA) WITH POLYSULFATED POLYSACCHARIDES

The present application is a continuation of U.S. patent application Ser. No. 13/983,406, filed Oct. 1, 2013, which was a U.S. National application based on Patent Cooperation Treaty Application No. PCT/AU2012/000091, filed on Feb. 2, 2012, which claims the benefit of Australian Application No. 2011900325, filed on Feb. 2, 2011, each of which is incorporated herein by reference in their entireties.

FIELD OF THE INVENTION

This invention relates to the medical use of sulphated polysaccharides for the treatment of a symptomatic bone marrow edema that may be present within the musculoskeletal system of a mammal.

BACKGROUND OF THE INVENTION

Bone marrow edema (BME) is a common multifactorial disorder which can occur in isolation and in association with several other medical conditions such as bone fractures, chronic use of steroid therapies (hypocortisonism), alcohol abuse, activated protein C (APC) resistance, prothrombin mutations or hyperhomocysteinaemia and rheumatoid arthritis. However, the appearance of bone marrow lesions in subjects with no known pre-existing disorders normally associated for bone marrow lesions has led to the classification of the condition as bone marrow edema syndrome (BMES). These types of BME are readily identified using magnetic resonance imaging (MRI) and are generally, but not invariably, accompanied by pain at rest and on undertaking physical activities [1-5]. Bone marrow edema has also been described as bone bruising, bone marrow contusions or bone marrow lesions and is frequently associated with a previous traumatic injury. For example 80% of patients who had sustained an acute anterior cruciate ligament (ACL) rupture of the knee joint or a similar post-traumatic joint injury exhibits the symptoms of pain emanating from the joint accompanied by regions of decreased signal intensity on T1-weighted MRI images and increased signal intensity on T2-weighted MRI images of the bone marrow spaces within the joint. Such MRIs images are consistent with localisation of interstitial fluid at site(s) within the bone marrow and are normally located directly adjacent to the areas where the highest contact injury was sustained [1-8]. With the ACL tears the subchondral bone marrow beneath the lateral femoral condyl and the posterior-lateral tibial plateau show the most significant MRI signals but other sites such as ligament insertion points which are also subjected to high tensional stress are may often be implicated. The size of the BME, as determined by MRI, has been reported to correlate with the intensity of activity and rest pain in the patient's knee joint. Moreover, it was noted from MRI follow-ups that a reduction in the size of the lesions was generally associated with a decrease in joint pain [1-8].

Although MRI is clearly the most reliable non-invasive methodology for the diagnosis of BME there is still ongoing debate as to the most appropriate MR pulse signals that would optimize the assessment of BME and achieve semi-quantification of its magnitude. This point is significant in regard to correlations of BME with indices of pain and joint function and how these parameters respond to various modalities of medical treatments. In a recently published study [9] the semi-quantitative assessment of subchondral BME lesions and subchondral cysts was compared using intermediate-weighted (IW) fat-suppressed (fs) spin echo and Dual Echo Steady State (DESS) sequences on a three Teslar (3T) MRI instrument. This investigation showed that the IW fs sequence identified more subchondral BME lesions and better qualified the extent of their size. While the DESS sequence improved the differentiation of subchondral BME lesions from subchondral cysts, the IW fs sequence was considered superior for the determination of lesion size [9]. The future application of intermediate-weighted (IW) fat-suppressed (fs) spin echo signal analysis coupled with higher resolution MRI instrumentation will undoubtedly serve to improve the quantification of BME and demonstrate the ubiquity of these lesions as the underlying cause of pain and functional disability in acute musculoskeletal disease and disorders.

In this respect subchondral or osteochondral injuries resulting in BME have also been recorded for the hip joint [10,11], foot and ankle joints [12-13] wrist joints [14] and vertebral bodies of the spinal column [15]. Interestingly, even low impact mechanical stress across joints can provoke a painful BME as was described for a patient who after a right knee medial collateral ligament sprain was prescribed the use of a lateral shoe wedge to correct for the medial compartment compression. After using the orthotic device for some weeks the patient presented with worsening pain and an increase in MRI lesion intensity. Discontinuation of the use of the insole reduced the pain and eliminated the BME [16].

Subchondral BME is not confined to synovial joints. The pubic symphysis is an amphi-arthrodial joint composed of two pelvic bones connected by a wedge shaped fibrocartilagenous disc. Beneath the interface of the fibrocartilagenous attachment to the bone plate resides the trabecular bone containing marrow. The trabecular bone in response to intense mechanical stresses, particularly tensional/rotational distraction, can undergo fatigue stress injuries leading to micro fractures and culminating in bone marrow edema. These types of pelvic injuries have been described collectively as groin pain, sports hernia (misnomer), athletic pubalgia, or osteitis pubis. It is seen most frequently in elite athletes, particularly long distance runners, soccer players, tennis players and Australian Rules football (AFL) players [17-19]. In the AFL studies it was shown that the incidence of pubic BME, as defined by the MRI signal intensities, was 77%. These bone marrow lesions were also associated with other MRI abnormalities including fibrocartilagenous cysts and secondary degenerative changes in the pubic symphysis. The MRI abnormalities correlated with a players past history of groin pain and tenderness of the pubic symphysis as was determined clinically [17]. It is significant that in a recent publication from the AFL it was reported that groin pain (including osteitis pubis) was one of the three most consistent causes of loss of player time in the AFL [20].

As already indicated an increase in interstitial fluid in subchondral bone marrow is an expression of BME. Such subchondral lesions, if untreated, can progress to bone necrosis and trabecular bone fractures and loss (localized osteoporosis) thereby weakening the underlying mechanical support for the overlaying articular cartilage. In addition, the subsequent disorganized repair of the damages subchondral bone structures can lead to thickening and stiffening of the subchondral bone plate rendering it less compliant to mechanical deformation on loading thereby conferring higher localized stresses on the adjacent articular cartilage thus accelerating its degeneration and progression to osteoarthritis (OA) [21, 22]. It would be expected therefore that there should exists a strong association between the topographical locations of subchondral BME and degenerative changes in the adjacent articular cartilage and the progression of OA. Support for this interpretation was provided in a recent study where, subchondral BME (reported as cysts) were detected by T1-weighted fat suppressed MRI in 47.7% of OA patients at entry. Over a two years follow-up period the severity of the cysts MRI hypersignal correlated with OA disease progression, as determined by cartilage volume loss in the medial compartment and the risk of receiving a total joint replacement [23]. Since many younger individuals with BME do not present with accompanying radiological or MRI evidence of OA it would seem that cartilage degeneration, which is considered as a characteristic pathological feature of OA joints, may arise as a secondary event to pre-existing BME. This conclusion is consistent with the early studies of Radin and colleagues who postulated that failure of subchondral trabecular bone (as exists in BME lesions) followed by its mechanical stiffening and reactivation of centers of secondary ossification (calcified cartilage) due to the disorganized repair was a primary cause of OA [21,22].

Additional support for the traumatic stress origin of BME or cysts has been provided by a study of racehorses [24]. The proximal metacarpal region of the performance racehorse is a frequent site of lameness. However, the origin of the pain has hitherto been difficult to diagnose precisely. Review of standing MRI images of the proximal metacarpus/distal carpus of a group of lame horses revealed extensive hyper intensity of the T2 gradient echo signals and a decrease in intensity of the T1 images in the third metacarpal bone that was consistent with a pre-existence of BME which from the literature cited herein, provided an explanation for the origin of the lameness [24].

The traditional medical treatments for symptomatic BME are rest and immobilization of the affected joints/anatomical region. The symptoms of pain and joint dysfunction may resolve spontaneously over 3-12 months, however, the quality of life of the patient during this period can be substantially diminished. With post-surgical patients and others who have BME identified by MRI analgesics or non-steroidal anti-inflammatory drugs (NSAIDs) are often prescribed. The rationale for the use of these drugs for this condition is that they will abrogate the symptoms of BME. However, there is no evidence that these drugs can achieve any beneficial effect since they have little or no therapeutic effect on the underlying pathophysiology responsible for BME. In some instances injections of corticosteroids have been used to treat BME, particularly in elite sports persons whose presence on the field of play is considered critical to the outcome of the game. On the basis of a well established literature [25-30] which has shown that NSAIDs and corticosteroids in particular, have negative effects on the metabolism of cartilage and bone, such medications would be contraindicated as they could hinder the natural tissue healing process. Moreover, corticosteroids can even exacerbate the problem because of their known pro coagulant, antifibrinolytic and osteoporotic inducing effects [28-30]. Such pharmacological activities would delay the clearing of thrombi from marrow spaces and arrest new bone deposition within the bone marrow lesion sites.

Heparin and structurally related polysulfated polysaccharides such as pentosan polysulfate, chitosan polysulfate, the fucans etc have been used for a number of years as anticoagulants [31-36]. Pentosan polysulfate (PPS) is a weaker anticoagulant than heparin [31,33,35] but has been used post-surgically and prophylactically as a thrombolytic agent [36]. However, when given via the oral and intrathecal routes, PPS is currently prescribed for the treatment of interstitial cystitis (inflammation of the bladder) [37-39]. PPS has also been proposed as a disease modifying drug for OA [40] and has demonstrated symptomatic relief in patients with OA [41, 42].

SUMMARY OF THE INVENTION

We have discovered that pentosan polysulfate (PPS) or a structurally related polysulfated polysaccharides when administration orally or systemically to a mammal with BME, as identified by the symptoms of pain and impaired function together with radiographic or MRI evidence of the localised collapse of trabecular bone and the presence of interstitial fluid in the bone marrow spaces of its musculoskeletal system, can therapeutically resolve the clinical symptoms and diminish the size of the BME. It has also been discovered by the inventor that (PPS) or a structurally related polysulfated polysaccharides can attenuate the local production of Tumor Necroses Factor Alpha (TNF-α) by cells in the BME which is postulated as the primary mediator of vascular and cellular changes that gives rise to the pain resulting from this and related medical conditions.

Accordingly, the present invention consists in a method for the treatment of bone marrow edema in a mammal comprising administering an effective amount of a polysulfated polysaccharide to a mammal in need of such treatment.

In another aspect, the present invention consists in a composition comprising an effective amount of a polysulfated polysaccharide and a pharmaceutically acceptable carrier for the treatment of bone marrow edema in a mammal.

In a further aspect, the present invention consists in the use of a polysulfated polysaccharide in the manufacture of a medicament for the treatment of bone marrow edema.

For purposes of clarity, bone marrow edema (BME) may be defined as follows: Occult injuries to the bone are often referred to as bone bruises or bone contusions and are readily demonstrated radiographically or by magnetic resonance imaging (MRI) as bone marrow cysts or bone marrow edema. These lesions appear as decreased signal intensity on MRI T1-weighted images and increased signal intensity on T2-weighted images. The MRI signals are thought to arise from increase concentration of interstitial fluids in areas of trabecular micro fractures and collapse within the bone marrow. These lesions may be the consequence of a direct blow to the bone, compressive forces of adjacent bones impacting on each other, or traction forces that occur during an avulsion injury such as at the site of attachment of a ligament or tendon to a bone. In other situations excessive rotational/shearing/extensional stresses as may occur in certain sporting activities may provoke the occurrence of edematous lesions within tissues as frequently seen in the pubic symphysis and diagnosed as "groin pain".

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

This invention is directed to treatments of mammals. However, unless specifically indicated in the description of the invention is to be understood to be applicable to humans and other mammals unless specifically indicated otherwise. Amongst other mammals may be mentioned domestic pets, such as cats and dogs, farm animals such as cattle, sheep, goats, horses, camels, etc as well as those mammals that usually exist in the wild but may be susceptible to treatment by virtue of such mammals being situated in zoos, wildlife parks and the like.

DESCRIPTION OF THE INVENTION

The polysulfated polysaccharide family can be considered to be any naturally occurring or semi-synthetic/synthetic polysulfated polysaccharide or a biologically active fragment thereof that contains two or more sugar rings to which one or more sulfate ester groups are covalently attached as exemplified by heparin and pentosan polysulfate.

Preparation of the polysulfate polysaccharide-metal complexes is described in detail in U.S. Pat. No. 5,668,116, the entire disclosure of which is incorporated herein by reference.

Further information relating to polysulfate polysaccharides and PPS can be found in WO 02/41901, the entire disclosure of which is incorporated herein by reference.

According to a preferred embodiment, the polysulfated polysaccharide to be used in this invention can be selected from, but are not limited to, naturally occurring high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

Therefore in one embodiment, the present invention consists in a method for the treatment of bone marrow edema in a mammal comprising administering an effective amount of a polysulfated polysaccharide, including salts thereof, selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclo dextrin and small sulfated compounds including, but are not limited to, inositol hexasulfate, to a mammal in need of such treatment.

In another embodiment, the present invention consists in a composition comprising an effective amount of a polysulfated polysaccharide including salts thereof, selected from the group consisting of naturally occurring high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate, and a pharmaceutically acceptable carrier for the treatment of bone marrow edema in a mammal.

In another embodiment, the present invention consists in the use of a polysulfated polysaccharide including salts thereof, selected from the group consisting of naturally occurring high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclo dextrin and small sulfated compounds including, but are not limited to, inositol hexasulfate, in the manufacture of a medicament for the treatment of bone marrow edema.

The preferred polysulfated polysaccharides include: pentosan polysulfate chondroitin polysulfate, chitosan polysulfate and heparin (high and low molecular weight fractions). See also British and US Pharmacopeia's for full description of heparin, fractionated heparin, and pentosan polysulfate structure and methods of identification.

Therefore in one embodiment, the present invention consists in a method for the treatment of bone marrow edema in a mammal comprising administering an effective amount of a polysulfated polysaccharide including salts thereof, selected from the group consisting of high molecular weight heparin, low molecular weight heparins, pentosan polysulfate, chondroitin polysulfate and chitosan polysulfate to a mammal in need of such treatment.

In another embodiment, the present invention consists in a composition comprising an effective amount of a polysulfated polysaccharide including salts thereof, selected from the group consisting of high molecular weight heparin, low molecular weight heparins, pentosan polysulfate, chondroitin polysulfate and chitosan polysulfate and a pharmaceutically acceptable carrier for the treatment of bone marrow edema in a mammal.

In another embodiment, the present invention consists in the use of a polysulfated polysaccharide including salts thereof, selected from the group consisting of high molecular weight heparin, low molecular weight heparins, pentosan polysulfate, chondroitin polysulfate and chitosan polysulfate in the manufacture of a medicament for the treatment of bone marrow edema.

The preferred polysulfated polysaccharides are pentosan polysulfate, the sodium salt of pentosan polysulfate (NaPPS), the magnesium salt of pentosan polysulfate (MgPPS), and/or the calcium salt of pentosan polysulfate (CaPPS).

Therefore in one embodiment, the present invention consists in a method for the treatment of bone marrow edema in a mammal comprising administering an effective amount of a polysulfated polysaccharide selected from the group consisting of pentosan polysulfate, the sodium salt of pentosan polysulfate (NaPPS), the magnesium salt of pentosan polysulfate (MgPPS), and/or the calcium salt of pentosan polysulfate (CaPPS) to a mammal in need of such treatment.

In another embodiment, the present invention consists in a composition comprising an effective amount of a polysulfated polysaccharide selected from the group consisting of pentosan polysulfate, the sodium salt of pentosan polysulfate (NaPPS), the magnesium salt of pentosan polysulfate (MgPPS), and/or the calcium salt of pentosan polysulfate (CaPPS) and a pharmaceutically acceptable carrier for the treatment of bone marrow edema in a mammal.

In another embodiment, the present invention consists in the use of a polysulfated polysaccharide including salts thereof, selected from the group consisting of pentosan polysulfate, the sodium salt of pentosan polysulfate (NaPPS), the magnesium salt of pentosan polysulfate (MgPPS), and/or the calcium salt of pentosan polysulfate (CaPPS) in the manufacture of a medicament for the treatment of bone marrow edema.

The most preferred polysulfated polysaccharide is the sodium pentosan polysulfate manufactured to the specifications lodged with the US FDA and European Community EMEA by Bene-PharmaChem GmbH & Co KG, Geretsried, Germany.

Therefore, in one embodiment, the present invention consists in a method for the treatment of bone marrow edema in a mammal comprising administering an effective amount of sodium pentosan polysulfate to a mammal in need of such treatment.

In another embodiment, the present invention consists in a composition comprising an effective amount of sodium pentosan polysulfate and a pharmaceutically acceptable carrier for the treatment of bone marrow edema in a mammal.

In another embodiment, the present invention consists in the use of sodium pentosan polysulfate in the manufacture of a medicament for the treatment of bone marrow edema.

The methods of manufacture, isolation and purification together with suitable carriers compositions and formulations are incorporated into the present application.

The term polysulfated polysaccharides and hypersulfated polysaccharide can be used interchangeably.

In the present invention, administration of PPS may be by injection using the intra-muscular (IM) and sub-cutaneous (SC) routes or it could be administered intra-venously (IV), intra-articularly (IA), peri-articularly, topically, via suppositories or orally. The injection route is preferred.

Therefore in one embodiment, the present invention consists in a method for the treatment of bone marrow edema in a mammal comprising administering by a method selected from injection using the intra-muscular (IM) or sub-cutaneous (SC) routes, intra-venously (IV), intra-articularly (IA), peri-articularly, topically, via suppositories or orally, an effective amount of a polysulfated polysaccharide including salts thereof, selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate, to a mammal in need of such treatment.

In another embodiment, the present invention consists in a composition comprising an effective amount of a polysulfated polysaccharide including salts thereof, selected from the group consisting of naturally occurring high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate, and a pharmaceutically acceptable carrier for the treatment of bone marrow edema in a mammal by administering the composition by a method selected from injection using the intra-muscular (IM) or sub-cutaneous (SC) routes, intra-venously (IV), intra-articularly (IA), peri-articularly, topically, via suppositories or orally.

In another embodiment, the present invention consists in the use of a polysulfated polysaccharide including salts thereof, selected from the group consisting of naturally occurring high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclo dextrin and small sulfated compounds including, but are not limited to, inositol hexasulfate, in the manufacture of a medicament for the treatment of bone marrow edema by administering the polysulfated polysaccharide by a method selected from injection by the intra-muscular (IM) or sub-cutaneous (SC) routes, intra-venously (IV), intra-articularly (IA), peri-articularly, topically, via suppositories or orally.

For the last 50 years or so Bene-PharmaChem has supplied their PPS in 1 ml glass ampoules containing 100 mg PPS/ml. Because of the ready availability of this sterile injectable product it is preferred to be used in the present invention.

Typically, about 1 to 2 mg/kg PPS, that is 1 to 2 ampoules of the Bene-PharmaChem injectable formulation is administered at each dosing for an average 70 kg individual. For heavier or lighter weighted individuals the PPS dose of 1-2 mg/kg would be adjusted accordingly. However, for convenience a single dose, for example of 200 mg PPS, dissolved in 2 ml of an appropriate buffer could be prepared as a 2 ml prefilled sterile syringe to avoid the necessity of opening the glass ampoules and filing a syringe before administering the injection.

For veterinary applications 10 ml vials containing 1000 mg PPS (or larger PPS amounts) could be used for multidose use from which are administered as about 2-3 mg/kg PPS by aspirating the required volume with a sterile syringe. Such dosing would be applicable, for example, in the treatment of horses where larger quantities of PPS are required because of the higher mass of these patients.

For human treatment, one regimen may comprise 5-10×1 ml ampoules or 3-6×2 ml prefilled syringes of the Bene-Pharmachem PPS administered once a day or thrice weekly depending on the severity of the pain experienced by the patient.

However, in some instances where a patient is experiencing high level pain, it is desirable to reach a therapeutic loading of the PPS as quickly as possible. This may necessitate, for example, the administration of about 1.0 mg/kg or more PPS daily until the pain is resolved.

For example, in one instance, the pain suffered by a patient was so debilitating that the patient received a total of 7 intramuscular injections (7×1 ml ampoules PPS [7×100 mg]) over a period of 7 day until the pain resolved. This equated to just over 1.0 mg/kg PPS daily.

When the PPS is administered by injection, this would normally be carried out in a clinical situation where the PPS would be administered by a nurse/doctor. In such circumstances, it is to be expected that 2-3 visits (injections) per week over several weeks would constitute a sufficient treatment regimen. The key to successful treatment is to administer sufficient PPS to the patient to achieve an optimum therapeutic dose in the vicinity of the tissue lesion. Since PPS accumulates in connective tissues, loading can be achieved over time, eg daily doses of 1 mg PPS/kg (100 mg PPS ampoule) for 7-10 days or 2 mg PPS/kg daily (2×100 ml PPS ampoules or 1×2 ml pre-filled syringe) over 4-5 days. Using such protocols the patient should eventually receive a total of about 200-2000 mg PPS, preferably about 1000 mg as course of treatment.

From a safety point of view the lower dose range (1-2 mg PPS/kg) over a longer period (5-10 days) is preferred. This is because PPS is a known anticoagulant and the basal APT may be elevated with the higher dose (>3 mg PPS/kg) which could potentially encourage bleeding of any open wounds.

For administration by IV infusion, the lower doses of 0.5-1 mg PPS/kg daily are preferred.

Whilst administration by injection is preferred, oral or topical formulations of PPS may be used as follow-up (maintenance dose) for the initial IM or SC PPS treatments. This would also be applicable to oral dosing using, for example, 100 mg capsules of NaPPS on a daily basis, the Calcium PPS derivative being preferred.

The Calcium PPS can be prepared by exchange of the sodium ions of the Bene NaPPS or by neutralization of the hydrogen form of PPS with calcium hydroxide.

It will be recognized by persons skilled in the art, that compositions suitable for administration by a variety of routes may be formulated by reference to standard textbooks in this field, such as Remington's Practice of Pharmacy. These compositions include by injection, oral (including tablets and capsules containing gastro-intestinal drug absorption extenders and enhancers), intravenous and the like.

The determination of the suitability of the treatment of the present invention or in other words the diagnosis of bone marrow edema may be established through the use of MRI together with the symptom of pain. For example, as decreased signal intensity on MRI T1-weighted images and increased signal intensity on T2-weighted images In order to better understand the nature of this invention, a number of examples will now be described.

EXAMPLES EMBODIMENTS

Figure 1A:
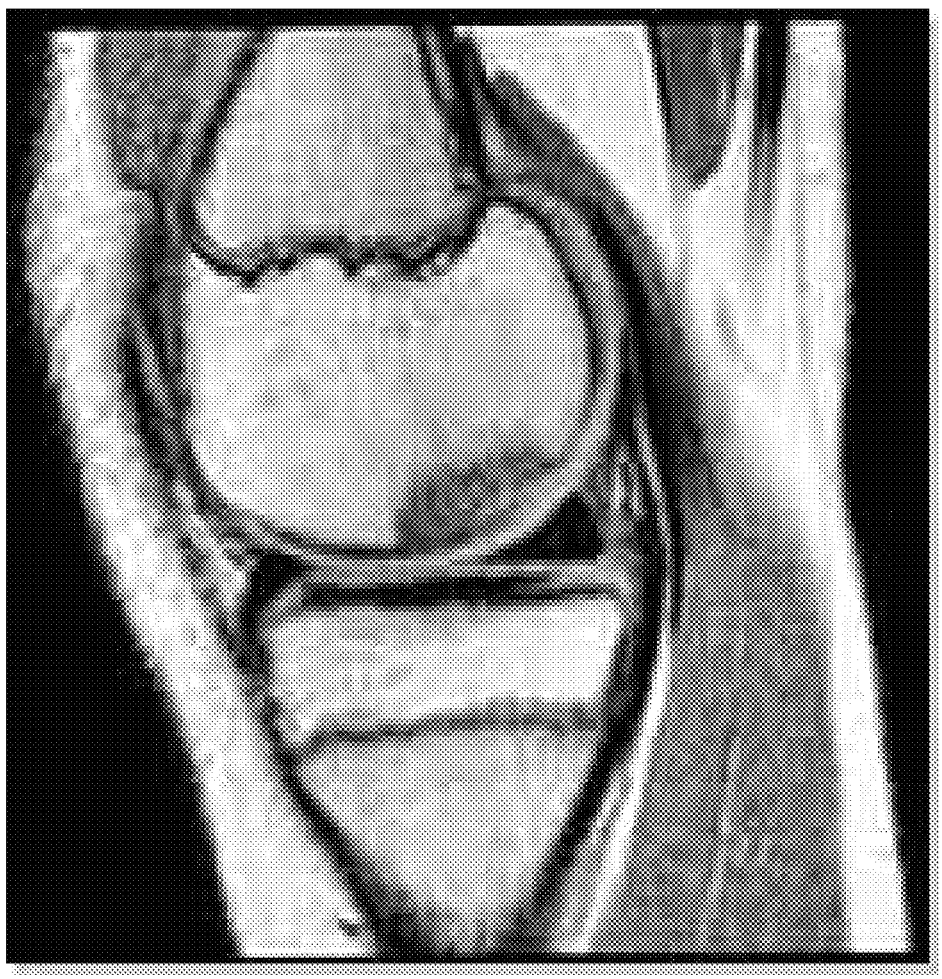
FIG. 1A is an MRI (T1 weighted scans) of subject PR showing the presence of bone marrow edema in the subchondral bone of the in left femoral condyle. Edema is evidenced by the reduced intensity of the signals in the semi-circular region beneath the articular cartilage. The MRI was taken 5 days following initial joint injury.

A. A method for the treatment of bone marrow edema in a mammal comprising administering an effective amount of a polysulfated polysaccharide including salts thereof, to a mammal in need of such treatment.

B. A composition comprising an effective amount of a polysulfated polysaccharide including salts thereof, and a pharmaceutically acceptable carrier for the treatment of bone marrow edema in a mammal.

C. Use of a polysulfated polysaccharide including salts thereof, in the manufacture of a medicament for the treatment of bone marrow edema.

D. A method according to Example Embodiment A, a composition according to Example Embodiment B or a use according to Example Embodiment C wherein the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

E. The method, the composition or the use according to Example Embodiment D wherein the polysulfated polysaccharide is selected from the group consisting of high molecular weight heparin, low molecular weight heparins, pentosan polysulfate, chondroitin polysulfate and chitosan polysulfate.

F. The method, the composition or the use according to Example Embodiment E wherein the polysulfated polysaccharide is selected from the group consisting of pentosan polysulfate, the sodium salt of pentosan polysulfate (NaPPS), the magnesium salt of pentosan polysulfate (MgPPS), and the calcium salt of pentosan polysulfate (CaPPS).

G. The method, the composition or the use according to Example Embodiment F wherein the polysulfated polysaccharide is sodium pentosan polysulfate.

H. The method, the composition or the use according to Example Embodiments A to G wherein treatment is by administering an injection by the intra-muscular (IM) or sub-cutaneous (SC) routes, intra-venously (IV), intra-articularly (IA), peri-articularly, topically, via suppositories or orally.

I. The method, the composition or the use according to Example Embodiment H wherein the treatment is by administering an injection.

J. The method, the composition or the use according to Example Embodiments A to I wherein the effective amount is about 1 to 2 mg/kg of the mammal per dose.

K. The method, the composition or the use according to Example Embodiment J wherein administration to a human is by dosing in a treatment regimen once daily or thrice weekly.

L. The method, the composition or the use according to Example Embodiment K wherein the total dose of polysulfated polysaccharide administered in the treatment regimen is about 200-2000 mg.

MODES FOR CARRYING OUT THE INVENTION

Examples

Example 1

Figure 1B:
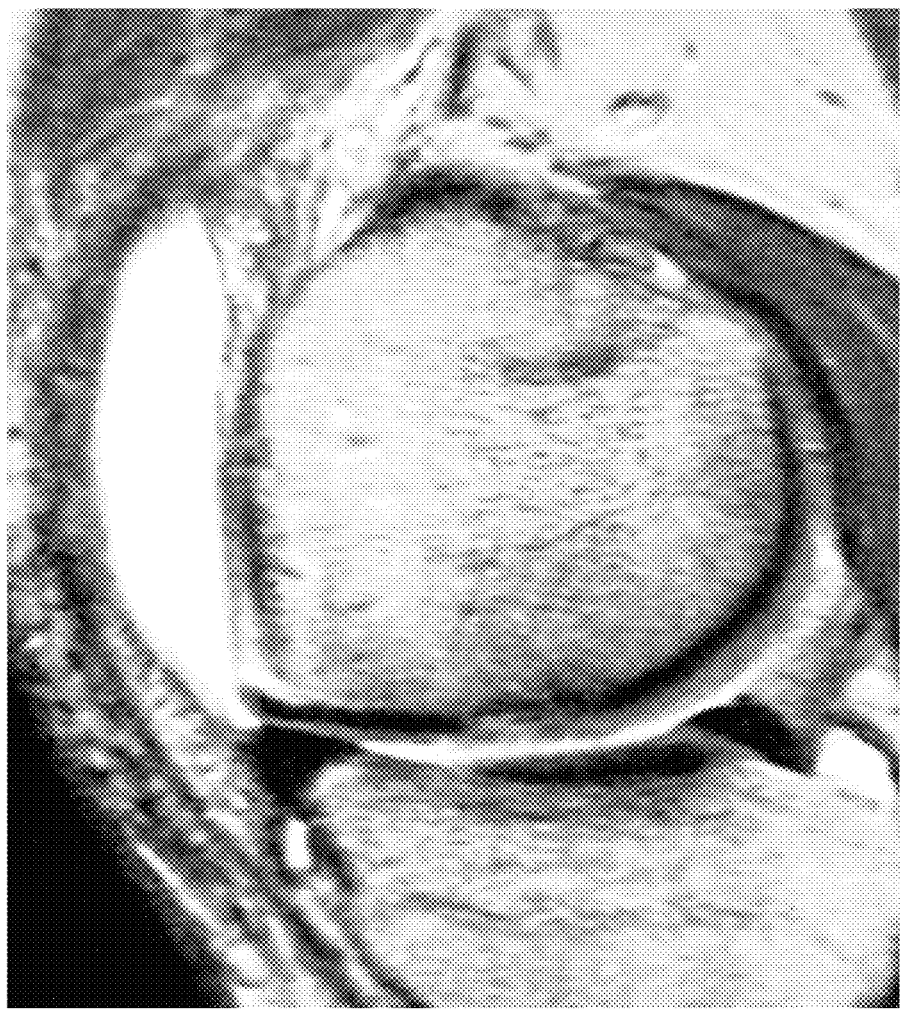
FIG. 1B is an MRI (T1 weighted scans) of subject PR taken one week after completing a course of 10×100 mg/ml IM injection of pentosan polysulfate. Note the absence of bone marrow edema in left femoral condyle. Magnification of MRI image shown is slightly higher than for FIG. 1A.

A male subject (PR) aged 53 years in good general health while jogging on the footpath stumbled and fell laterally striking the pavement with his right knee. Next day the knee was swollen and extremely painful and when examined by a medical practitioner was diagnosed as avulsion of the collateral ligament attachment to tibial bone. This diagnosis was confirmed by MRI that also showed the presence of a large subchondral BME in the femoral subchondral bone (FIG. 1A). Five days after sustaining the injury surgical repair was undertaken to re-attach the free ligament bone insertion to the tibia. However the knee pain persisted thereafter and was not relieved by use of analgesics or NSAIDs. Five weeks after the surgery a course of PPS, 100 mg/ml injections administered intramuscularly twice weekly for 5 weeks was initiated (total of 10 injections). After receiving the 6th injection, the pain and joint swelling had disappeared and one week after completion of the PPS course of injections the joint was again reviewed by T1 weighted MRI. As is evident from FIG. 1B the BME present at the onset of PPS treatment had completely resolved following the administration of PPS.

Example 2

A retired female figure ice-skater (JP), 26 years of age and in good health, fell heavily on her ankle while moving house. The ankle showed extensive bruising and she rested the joint for one week and to some extent the pain was relieved. However, the pain was still intense on weight-bearing and JP consulted her orthopaedic foot specialist who referred her to a physiotherapist for treatment. After 6 weeks of physiotherapy the swelling and bruising had declined but pain originating from the ankle joint was still present, particularly on weight-bearing. A second visit to the orthopaedic specialist resulted in a MRI scan that revealed BME in the impacted bones of the joint. Although JP was advised to continue physiotherapy by her orthopaedic specialist, the pain still persisted but would have been resolved by a course of 6 subcutaneous injections of PPS (100 mg) over 10 days.

Example 3

A healthy 70 year-old male (PG) with genu varum of approximately 5 degrees slipped on a step at an airport terminal while rushing to catch an international flight such that his left foot made an unexpected high impact with the ground. After arriving at his destination late that evening, PG retired for the night but was woken in the early hours of the morning with intense throbbing pain originating from the medial compartment of his left knee joint. Oral analgesics every 3 hours failed to significantly diminish the knee pain and next day PG commenced a course of intra-muscular injections of PPS (100 mg) administered daily. Following the 5th injection the knee pain had substantially subsided and was completely resolved after the 7th injection. The debilitating joint pain experienced by this individual following the sub-chondral bone contusion (BME) incurred by the sudden high mechanical impart did not re-occur in subsequent months following the PPS course of therapy which was consistent with the resolution of the BME.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

REFERENCES

1. Nakame A, Engebretsen L, Bahr R, Krosshaug T, Ochi M. Natural history of bone bruises after acute knee injury: clinical outcome and histopathological findings. Knee Surg Sports Traumatol Arthrose 2006; 14:1252-1258.
2. Boks S S, Vroegindeweij D, Koes B W, Bernsen R M, Hunink M G, Bierma-Zeinstra S M. Clinical consequences of posttraumatic bone bruise in the knee. Am J Sports Med 2007; 35(6):990-5.
3. Gönç U, Kayaalp A, Irgit K. Bone bruises of the knee. Acta Orthop Traumatol Turc 2007; 41 Suppl 2:98-104.
4. Thiryayi W A, Thiryayi S A, Freemont A J. Histopathological perspective on bone marrow oedema reactive bone change and haemorrhage. Eur J Radiol 2008; 67(1):62-7.
5. Unay K, Poyanli O, Akan K, Guven M, Demircay C. The relationship between bone marrow edema size and knee pain. Knee Surg Sports Traumatol Arthrosc 2009; 17(11): 1298-304.
6. Theologis A A, Kuo D, Cheng J, Bolbos R I, Carballido-Garnio J, Ma C B, Li X. Evaluation of bone bruises and associated cartilage in anterior cruciat ligament-injured and -reconstructed knees using quantitative 1 tesla magnetic resonance imaging: 1-year cohort study. Arthroscopy 2011; 27(1):65-76.
7. Davies N H, Niall D, King L J, Lavelle J, Healy J C. Magnetic resonance imaging of bone bruising in the acutely injured knee—short-term outcome. Clin Radiol 2004; 59(5):439-45.
8. Szkopek K, Warming T, Neergaard K, et al. Pain and Knee function in relation to degree of bone bruise after acute anterior cruciate ligament rupture. Scand J Med Sci Sports 2011; April 8, doi: 10.1111/j.1600-0838.2011.01297.x. [Epub ahead of print].
9. Hayashi D, Guermazi A, Kwok C K, et al. Semiquantitative assessment of subchondral bone marrow edema-like lesions and subchondral cysts of the knee at 3T MRI: A comparison between intermediate-weighted fat-suppressed spin echo and Dual Echo Steady State sequences. BMC Musculoskeletal Disorders 2011; 12: 198-206.
10. Hoffman S. The painful bone marrow edema syndrome of the hip joint. Wien Klin Wochenschr. 2005; 117(4): 111-20.
11. Koo H-K, Ahn I-O, Kim R, Song H-R, Jeong S-T, Na J-B, Kim Y-S Cho S-H. Bone Marrow Edema and associated pain in early stage osteonecrosis of the femoral head: prospective study with serial MR images. Radiology 1999; 213:715-22.
12. O'Loughlin P F, Heyworth B E, Kennedy J G. Current concepts in the diagnosis and treatment of osteochondral lesions of the ankle. Am J Sports Med 2010; 38:392-404.
13. Orr J D, Sabesan V, Major N, Nunley J. Painful bone marrow edema syndrome of the foot and ankle. Foot Ankle Int 2010; 31(11):949-53.
14. Fatiadou A, Patel A, Morgan T, Karantanas A H. Wrist injuries in young adults: The diagnostic impact of C T and MRI. Eur J Radiol. 2010 Jun. 14.
15. Voormolen M H J, van Rooij W J, van der Graaf Y, et al. Bone marrow edema in osteoporotic vertebral compression fractures after percutaneous vertebroplasty and relation with clinical outcome. American J Neuroradiology. 2006; 27: 983-988.
16. Chaler J, Torra M, Dolz J L, Müller B, Garreta R. Painful lateral knee condyle bone marrow edema after treatment with lateral wedged insole. Am J Phys Med Rehabil 2010; 89(5):429-33.
17. Verrall G M, Slavotinek J P, Fon G T. Incidence of pubic bone marrow oedema in Australian Rules football players: relation to groin pain. Br J Sports Med 2001; 35:28-33.
18. Lovell G, Galloway H, Hopkins W, Harvey A. Osteitis pubis and assessment of bone marrow edema at the pubic synphysis with MRI in an elite junior male soccer squad. Clin J Sport Med 2006; 16(2):117-22.
19. Omar I M, Zoga A C, Kavanagh E C, Koulouris G, Bergin D, Gopez A G, Morrison W B, Meyers W C. Athletic pubalgia and "sports hernia": optimal M R imaging technique and findings. Radiographics 2008; 28(5): 1415-38.
20. Orchard J, Seward H. 2009 Injury Report—Australian Football League. Wednesday 12 May 2010.
21. Radin El and Paul I L. The importance of bone in sparing articular cartilage from impact. Clin Orthop Related Res. 1971; 78: 342-344.
22. Radin E R, Paul I L, Rose R M. The pathogenesis of primary osteoarthritis. Lancet 1972; June 24: 1395-1396.

23. Tanamas S K, Wluka A E, Pelletier J-P, Martel-Pelletier J, Abram F, Wang Y U, Cicuttini F. The association between subchondral bone cysts and tibial cartilage volume and risk of joint replacement in people with knee osteoarthritis: a longitudinal study. Arthritis Research and Therapy 2010; 12:R58.

24. Powell S E, Ramzan P H, Head M J, Shepherd M C, Baldwin G I, Steven W N. Standing magnetic resonance imaging detection bone marrow oedema-type signal pattern associated with subcarpal pain in 8 racehorses: a prospective study. Equine Vet J 2010; 42(1)10-7.

25. Brandt K D. Should nonsteroidal anti-inflammatory drugs be used to treat osteoarthritis? Rheumatic Disease Clinics of North America 1993; 19:29-44.

26. Huskisson E C, Berry H, Gishen P. Jubb R W, Whitehead J. Effects of anti-inflammatory drugs on the progression of osteoarthritis of the knee. Journal of Rheumatology 1995; 22:1941-6.

27. McKenzie L S, Horsburgh B A, Ghosh P, Taylor T K F. Effect of anti-inflammatory drugs on sulphated glycosaminoglycan synthesis in aged human articular cartilage. Ann rheum Dis 1976; 35(6):487-497.

28. Werb Z. Biochemical actions of glycocorticoids on macrophages in culture. Specific in activator secretion and effects on other metabolic functions. JEM 1978; 147(6): 1695-1712.

29. Romas E. Corticosteroid-induced osteoporosis and fractures. Australian Prescriber 2008; 31(2):45-49.

30. Kream B. Clinical and basic aspects of glucocorticord actions in bone. in Principle of Bone Biology Vol 1 Chapter 44; Eds: Bilezikian, Raisz L G, Roc G A. Elsevier B V Netherlands 2008 Academic Press New York.

31. Scully M F, Weerasinghe K M, Ellis V, Djazaeri B, Kakkar V V. Anticoagulant and antiheparin activities of a pentosan polysulphate. Thrombosis Research 1983; 31(1):87-97.

32. Krupinski K, Breddin H K, Casu B. Anticoagulant and antithrombotic effects of chemically modified heparins and pentosan polysulfate. Haemostasis 1990; 20(2):81-92.

33. Shanmugam M, Mody K H. Heparinoid-active sulphated polysaccharides from marine algae as potential blood anticoagulant agents. Current Science 2000; 79(12): 1672-1683.

34. Vongchan P, Sajomsang W, Kasinrerk W, Subyen D, Kongrawelert P. Anticoagulant activities of the chitosan polysulfate synthesized from marine crab shell by semi-heterogeneous conditions. Science Asia 2003; 29:115-120.

35. Vinazzer H. Prevention of recurrence of cerebrovascular thromboses. A randomized comparative study acetylsalicylic acid and sodium pentosan polysulfate. Fortschr Med 1987; 105(5):79-85.

36. Losonczy H, David M, Nagy I. Effect of pentosan polysulfate on activated partial thromboplastin time, thrombin time, euglobulin clot lysis and tissue-type plasminogen activator and plasminogen activator inhibitor activities in patients with thromboembolic disease. Semin Thromb Hemost 1991; 17(4):394-8.

37. Anderson V R, Perry C M. Pentosan polysulfate: a review of its use in the relief of bladder pain or discomfort in interstitial cystitis. Drugs 2006; 66(6):821-35.

38. Dimitrakov J, Kroenke K, Steers W D, Berde C, Zurakowski D, Freeman M R, Jackson J L. Pharmacologic management of painful bladder syndrome/interstitial cystitis: a systematic review. Arch Intern Med 2007; 167(18): 1922-9.

39. Davis E L, El Khoudary S R, Talbott E O, Davis J, Regan L R. Safety and efficacy of the use of intravesical and oral pentosan polysulfate sodium for interstitial cystitis: a randomized double-blind clinical trial. J Urol 2008; 179 (1):177-85.

40. Ghosh P. The pathobiology of osteoarthritis and the rationale for the use of pentosan polysulfate for its treatment. Sem Arthritis Rheum 1999; 28:211-67.

41. Ghosh P, Edelman J, March L, Smith M. Effects of pentosan polysulfate in osteoarthritis of the knee: a randomized, double-blind, placebo-controlled pilot study. Current Ther Research 2005; 6:552-71.

42. Kumagai K, Shirabe S, Miyata N et al. Sodium pentosan polysulfate resulted in cartilage improvement in knee osteoarthritis—an open clinical trial. BMC Clin Pharm 2010; 10:1-9.

The invention claimed is:

1. A method for the treatment of bone marrow edema in a mammal not suffering from osteoarthritis, comprising administering intra-articularly or peri-articularly from about 1 mg/kg to about 2 mg/kg per dose of a polysulfated polysaccharide selected from the group consisting of pentosan polysulfate, the sodium salt of pentosan polysulfate (NaPPS), the magnesium salt of pentosan polysulfate (MgPPS), and the calcium salt of pentosan polysulfate (CaPPS) to a mammal in need of such treatment.

2. The method according to claim 1 wherein the polysulfated polysaccharide is sodium pentosan polysulfate.

3. The method according to claim 1, wherein treatment is intra-articularly (IA).

4. The method according to claim 1, wherein the treatment is peri-articularly.

5. The method according to claim 1, wherein administration is to a human and is by dosing in a treatment regimen once daily, twice weekly, or thrice weekly.

6. The method according to claim 1, wherein the total dose of polysulfated polysaccharide administered in the treatment regimen is from about 200 mg to about 2000 mg.

* * * * *